United States Patent
Davidsen (10) Patent No.: US 7,927,280 B2
(45) Date of Patent: Apr. 19, 2011

(54) CURVED 2-D ARRAY ULTRASOUND TRANSDUCER AND METHOD FOR VOLUMETRIC IMAGING

(75) Inventor: Richard Davidsen, Everett, WA (US)

(73) Assignee: Koninklijke Philips Electronics N.V., Eindhoven (NL)

(*) Notice: Subject to any disclaimer, the term of this patent is extended or adjusted under 35 U.S.C. 154(b) by 547 days.

(21) Appl. No.: 11/996,991

(22) PCT Filed: Jul. 24, 2006

(86) PCT No.: PCT/IB2006/052537
§ 371 (c)(1),
(2), (4) Date: Jan. 28, 2008

(87) PCT Pub. No.: WO2007/017781
PCT Pub. Date: Feb. 15, 2007

(65) Prior Publication Data
US 2008/0221454 A1    Sep. 11, 2008

Related U.S. Application Data

(60) Provisional application No. 60/706,208, filed on Aug. 5, 2005.

(51) Int. Cl.
*A61B 8/00* (2006.01)
(52) U.S. Cl. ......................... 600/447; 600/459
(58) Field of Classification Search .......... 600/437–466; 73/625–626; 367/178; 128/915–916
See application file for complete search history.

(56) References Cited

U.S. PATENT DOCUMENTS

| | | | |
|---|---|---|---|
| 4,470,308 A * | 9/1984 | Hayakawa et al. | 73/642 |
| 4,747,192 A * | 5/1988 | Rokurota | 29/25.35 |
| 5,027,820 A * | 7/1991 | Pesque | 600/443 |
| 5,060,651 A * | 10/1991 | Kondo et al. | 600/443 |
| 5,148,810 A * | 9/1992 | Maslak et al. | 600/447 |
| 5,229,933 A * | 7/1993 | Larson, III | 600/459 |
| 5,798,461 A * | 8/1998 | Banta et al. | 73/625 |
| 6,013,032 A * | 1/2000 | Savord | 600/443 |
| 6,055,861 A * | 5/2000 | Banta et al. | 73/626 |
| 6,102,860 A | 8/2000 | Mooney | |
| 6,530,885 B1 * | 3/2003 | Entrekin et al. | 600/437 |
| 6,671,227 B2 * | 12/2003 | Gilbert et al. | 367/138 |
| 7,637,869 B2 * | 12/2009 | Sudol | 600/437 |
| 2003/0216645 A1 | 11/2003 | Xin et al. | |

FOREIGN PATENT DOCUMENTS

| | | |
|---|---|---|
| EP | 1214909 A | 6/2002 |
| WO | 03003045 A2 | 1/2003 |

* cited by examiner

*Primary Examiner* — Francis Jaworski
(74) *Attorney, Agent, or Firm* — W. Brinton Yorks, Jr.

(57) ABSTRACT

An ultrasound imaging system includes an imaging probe having an array of transducer elements that is flat and relatively elongated in the azimuth direction and is curved outwardly in the elevation direction. As a result, when the transducer elements are scanned in a step-wise manner, the acoustic pattern of the probe diverges in the elevation direction. The probe therefore provides a large field of view in the near field despite using relatively few transducer elements. The probe also includes sub-array beamformers to delay signals transmitted and received from the transducer elements in respective sub-arrays. The received signals are coupled to an imaging system which includes a signal path that processes the received signals into signals corresponding to a volumetric image. A display coupled to the signal path can then show a volumetric image of anatomical features in a volumetric region adjacent the array of transducer elements.

11 Claims, 5 Drawing Sheets

CURVED 2-D ARRAY ULTRASOUND TRANSDUCER AND METHOD FOR VOLUMETRIC IMAGING

CROSS REFERENCE TO RELATED APPLICATION

This application claims the benefit of U.S. provisional application Ser. No. 60/706,208 filed Aug. 5, 2005, which is incorporated herein.

This invention relates to medical ultrasound imaging and, more particularly, to an ultrasound transducer that is adapted for volumetric imaging of relatively large shallow anatomical features.

Various noninvasive diagnostic imaging modalities are capable of producing cross-sectional images of organs or vessels inside the body. An imaging modality that is well suited for such noninvasive imaging is ultrasound. Ultrasound diagnostic imaging systems are in widespread use by cardiologists, obstetricians, radiologists and others for examinations of the heart, a developing fetus, internal abdominal organs and other anatomical structures. These systems operate by transmitting waves of ultrasound energy into the body, receiving ultrasound echoes reflected from tissue interfaces upon which the waves impinge, and translating the received echoes into structural representations of portions of the body through which the ultrasound waves are directed.

In conventional ultrasound imaging, objects of interest, such as internal tissues and blood, are scanned using planar ultrasound beams or slices. A linear array transducer is conventionally used to scan a thin slice by narrowly focusing the transmitted and received ultrasound in an elevation direction and steering the transmitted and received ultrasound throughout a range of angles in an azimuth direction. A transducer having a linear array of transducer elements, which is also known as a one-dimensional array, can operate in this manner to provide a two-dimensional image representing a cross-section through a plane that is perpendicular to a face of the transducer for B-mode imaging.

Linear arrays can also be used to generate three-dimensional images, which are also known as "volumetric" images, by translating the one-dimensional array linearly in the elevation direction or by sweeping the array through a range of angles extending in the elevation direction. Volumetric ultrasound images can also be conventionally obtained by using a two-dimensional array transducer to steer the transmitted and received ultrasound about two axes.

The primary limitation of using one-dimensional arrays for volumetric imaging is the need to physically move the array in order to obtain images. This requirement imposes upon an ultrasound system the need to track the location or angle of the one-dimensional array, either by physically tracking the movement of the array or by electrically processing the image signals. Furthermore, it can require a substantial period of time to acquire a volumetric image because of the need to move the array and process the ultrasound return signals received at each location or angle of the array. The primary advantage of using one-dimensional arrays for ultrasound imaging is that the area that can be imaged even in the near field is limited only by the number of elements in the array and the area over which the array is moved.

Another approach to using a one-dimensional array to obtain information about anatomical structures in a three-dimensional volume is described in U.S. Pat. No. 5,305,756. As described therein, transmitted and received ultrasound is focused in the azimuth direction AZ, but divergent in the elevation direction to generate a series of fan-shaped beams. The ultrasound is sequentially transmitted and received from each element in the linear array to form a sequence of fan-shaped beams that insonify a volumetric region. In the center of the insonified volumetric region is a plane of projection. All of the echoes in the volumetric region at each range are projected as a point onto the plane of projection at the corresponding range. The resulting image presents a two-dimensional projection of the entire volumetric region because the transducer acoustically integrates all echoes at each range.

Although the imaging technique described in U.S. Pat. No. 5,305,756 has the advantage of not requiring physical scanning of the array, it has the significant disadvantage of not actually providing a true three-dimensional volumetric image. As a result, it may not accurately show anatomical features in a volumetric region beneath array. For example, points at the same depth will appear to span a range of depths on the projection since the points will not lie on a constant range locus from the transducer. Conversely, an anatomical structure that spans a range of depths can appear on the projection to be at a single depth. Also, the projected image may not resolve anatomical structures that lie along the same constant range locus from the transducer. For example, a structure that occupies only a small portion of the constant range locus may be obscured by other anatomical structures that also lie on the constant range locus.

The use of two-dimensional arrays for volumetric imaging has many advantages, including the lack of any need to physically scan the array and the ability to provide true three-dimensional images. As a result, ultrasound images can be obtained more rapidly using a two-dimensional array than can be obtained using a one-dimensional array. However, the number of transducer elements in a two-dimensional array can increase to an impractically large number when attempts are made to increase the size or aperture of the array in order to provide a large field of view. In particular, some of the challenges presented by the use and design of arrays having 10,000 or more elements are the design of suitable circuitry, such as application specific integrated circuits, management of the large amount of heat generated by so many tightly packed transducer elements, the size of the cable that would be required to couple the signals from these large number of transducer elements to an ultrasound imaging system, acoustic flatness requirements, and general fabrication difficulties. As a result of these difficulties, the number of elements in conventional two-dimensional ultrasound arrays have generally been limited to about 3,000 elements. For this reason, conventional two-dimensional ultrasound arrays provide a relatively small imaging aperture.

The relatively small imaging aperture that can be achieved with conventional two-dimensional arrays has limited their use to specific applications, such as cardiology, that have small access areas and modest field of view requirements in the near field, i.e., at shallow depths close to the face of the array. These relatively small aperture arrays can image over a larger field of view in the far field because the transmitted and received ultrasound can be steered in diverging directions. However, certain applications, such as obstetrical imaging, require imaging a relatively large field of view in the near field. Conventional two-dimensional arrays do not have a large enough aperture to be useful in these applications for the reasons previously indicated.

There is therefore a need for a two-dimensional ultrasound array for true volumetric imaging that can achieve a large field of view in the near field without the use of an impractically large number of transducer elements.

In accordance with the principles of the present invention an ultrasound imaging system includes an ultrasound imaging probe, an ultrasound signal path connected to the probe through a communication link, and a display. The ultrasound imaging probe transmits beams that are substantially parallel or divergent in an azimuth direction and divergent in an elevation direction. This beam pattern may be caused by a lens which causes the beams to diverge in the elevation direction or by physical curvature of the array in the elevation direction. An array of transducer elements has rows extending in the azimuth direction and columns extending in the elevation direction. The ultrasound signal path applies transmit signals to and receives signals from the transducer elements in the ultrasound imaging probe through the communications link. The ultrasound signal path combines the signals received from the transducer elements into image signals corresponding to a volumetric image of anatomical structures in a volumetric region adjacent the ultrasound imaging probe. The volumetric image is then shown on the display. The transducer elements in the imaging probe are preferably scanned in a stepping manner from one row or group of rows or one column or group of columns to the next. The imaging probe also preferably includes a plurality of sub-array beamformers coupled to respective sub-arrays of the transducer elements. Each of the sub-array beamformers is operable to apply transmit signals to the transducer elements in the respective sub-array responsive to the transmit signals received from the ultrasound imaging path. Each of the sub-array beamformers is also operable to steer beams in non-orthogonal directions with respect to the surface of the array so that the divergent beams will scan a wide field of view in the near field. The processed signals from each of the sub-arrays are then combined into a composite receive signal that is coupled through the communications link to the ultrasound imaging path.

Figure 1:
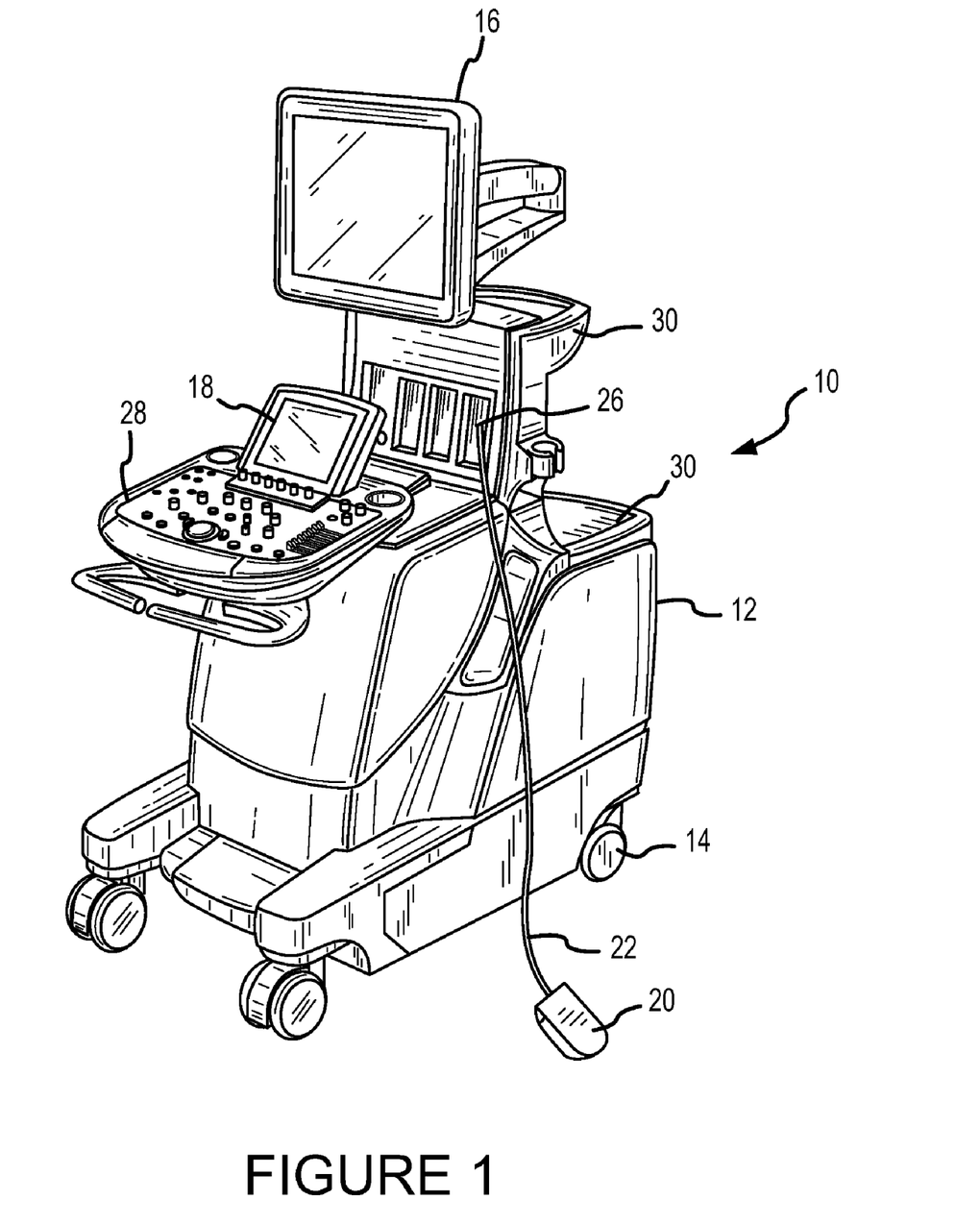
FIG. 1 is an isometric view of an ultrasound imaging system according to one example of the invention.

An ultrasound imaging system 10 according to one example of the invention is illustrated in FIG. 1. The system 10 includes a chassis 12 containing most of the electronic circuitry for the system 10. The chassis 12 is mounted on a cart 14, and a display 16 is mounted on the chassis 12. An imaging probe 20 is connected through a cable 22 to one of three connectors 26 on the chassis 12. As explained in greater detail below, the probe 20 includes an two-dimensional ultrasound imaging array that uses relatively few transducer elements yet is able to provide a large field of view in the near field. The use of relatively few transducer elements and other techniques that subsequently will be described allow the cable 22 to be relatively thin so that the cable 22 does not restrict the ability to easily manipulate the imaging probe 20. However, there is an advantage substantially reducing the number of signals that must be coupled from the probe 20 to the chassis 12 even if the signals are coupled by means other than the cable 22. For example, if the signals are coupled from the probe 20 to the chassis 12 by wireless radio or infra-red, the reduced number of signals reduces the number of required wireless channels and/or the wireless bandwidth.

With further reference to FIG. 1, the chassis 12 includes a keyboard and controls, generally indicated by reference numeral 28, for allowing a sonographer to operate the ultrasound system 10 and enter information about the patient or the type of examination that is being conducted. At the back of the control panel 28 is a touchscreen display 18 on which programmable softkeys are displayed for supplementing the keyboard and controls 28 in controlling the operation of the system 10.

In operation, the imaging probe 20 is placed against the skin of a patient (not shown) and held stationery to acquire an image of blood or tissues in a volumetric region beneath the skin. The large field of view of the imaging probe 20 in the near field makes the system 20 particularly useful for certain fields, such as obstetrics, where volumetric imaging has not previously been practical. The volumetric image is presented on the display 16, and it may be recorded by a recorder (not shown) placed on one of the two accessory shelves 30. The system 10 may also record or print a report containing text and images. Data corresponding to the image may also be downloaded through a suitable data link, such as the Internet or a local area network. In addition to using the two-dimensional probe 20 to show a volumetric image on the display, the ultrasound imaging system may also provide other types of images using the probe 20, and it may accept other types of probes (not shown) to provide other types of images.

Figure 2:
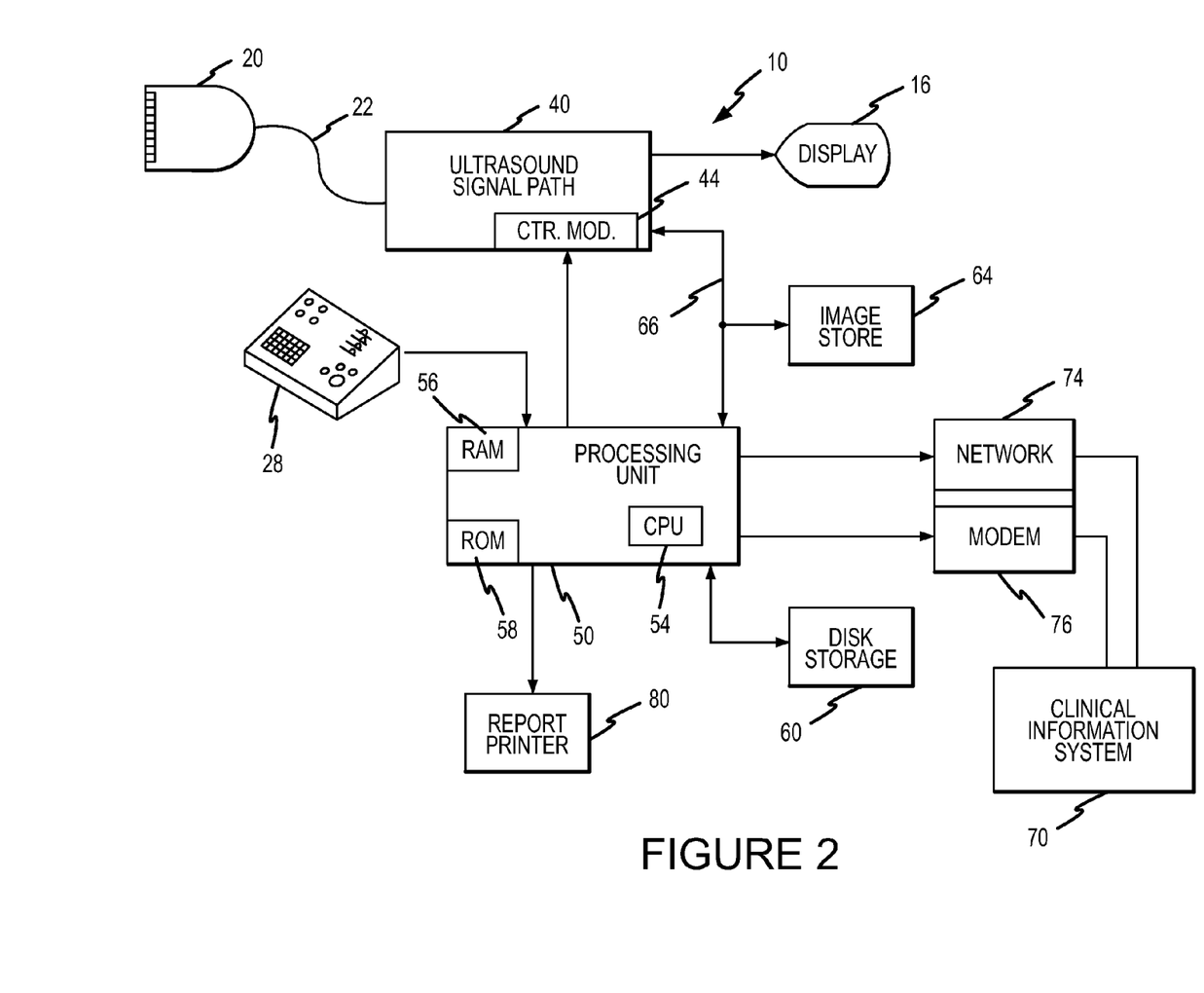
FIG. 2 is a block diagram of the electrical components used in the ultrasound imaging system of FIG. 1.

The electrical components of the ultrasound imaging system 10 are illustrated in FIG. 2. As mentioned above, the ultrasound imaging probe 20 is coupled by the cable 22 to one of the connectors 26, which are connected to an ultrasound signal path 40 of conventional design. As is well-known in the art, the ultrasound signal path 40 includes a transmitter (not shown) coupling electrical signals to the probe 20, an acquisition unit (not shown) that receives electrical signals from the probe 20 corresponding to ultrasound echoes, a signal processing unit (not shown) that processes the signals from the acquisition unit to perform a variety of functions such as isolating returns from specific depths or isolating returns from blood flowing through vessels, and a scan converter (not shown) that converts the signals from the signal processing unit so that they are suitable for use by the display 16. The processing unit in this example is capable of processing both B mode (structural) and Doppler signals for the production of various B mode and Doppler volumetric images, including spectral Doppler volumetric images. The ultrasound signal path 40 also includes a control module 44 that interfaces with a processing unit 50 to control the operation of the above-described units. The ultrasound signal path 40 may, of course, contain components in addition to those described above, and, in suitable instances, some of the components described above may be omitted.

The processing unit 50 contains a number of components, including a central processor unit ("CPU") 54, random access memory ("RAM") 56, and read only memory ("ROM") 58, to name a few. As is well-known in the art, the ROM 58 stores a program of instructions that are executed by the CPU 54, as well as initialization data for use by the CPU 54. The RAM 56 provides temporary storage of data and instructions for use by the CPU 54. The processing unit 50 interfaces with a mass storage device such as a disk drive 60 for permanent storage of data, such as data corresponding to ultrasound images obtained by the system 10. However, such image data is initially stored in an image storage device 64 that is coupled to a signal path 66 extending between the ultrasound signal path 40 and the processing unit 50. The disk drive 60 also preferably stores protocols which may be called up and initiated to guide the sonographer through various ultrasound exams.

The processing unit 50 also interfaces with the keyboard and controls 28. The keyboard and controls 28 may also be manipulated by the sonographer to cause the ultrasound system 10 to produce automatically generated reports at the conclusion of an examination. The processing unit 50 preferably interfaces with a report printer 80 that prints reports containing text and one or more images. The type of reports provided by the printer 80 depends on the type of ultrasound examination that was conducted by the execution of a specific protocol. Finally, as mentioned above, data corresponding to the image may be downloaded through a suitable data link, such as a network 74 or a modem 76, to a clinical information system 70 or other device.

Figure 3:
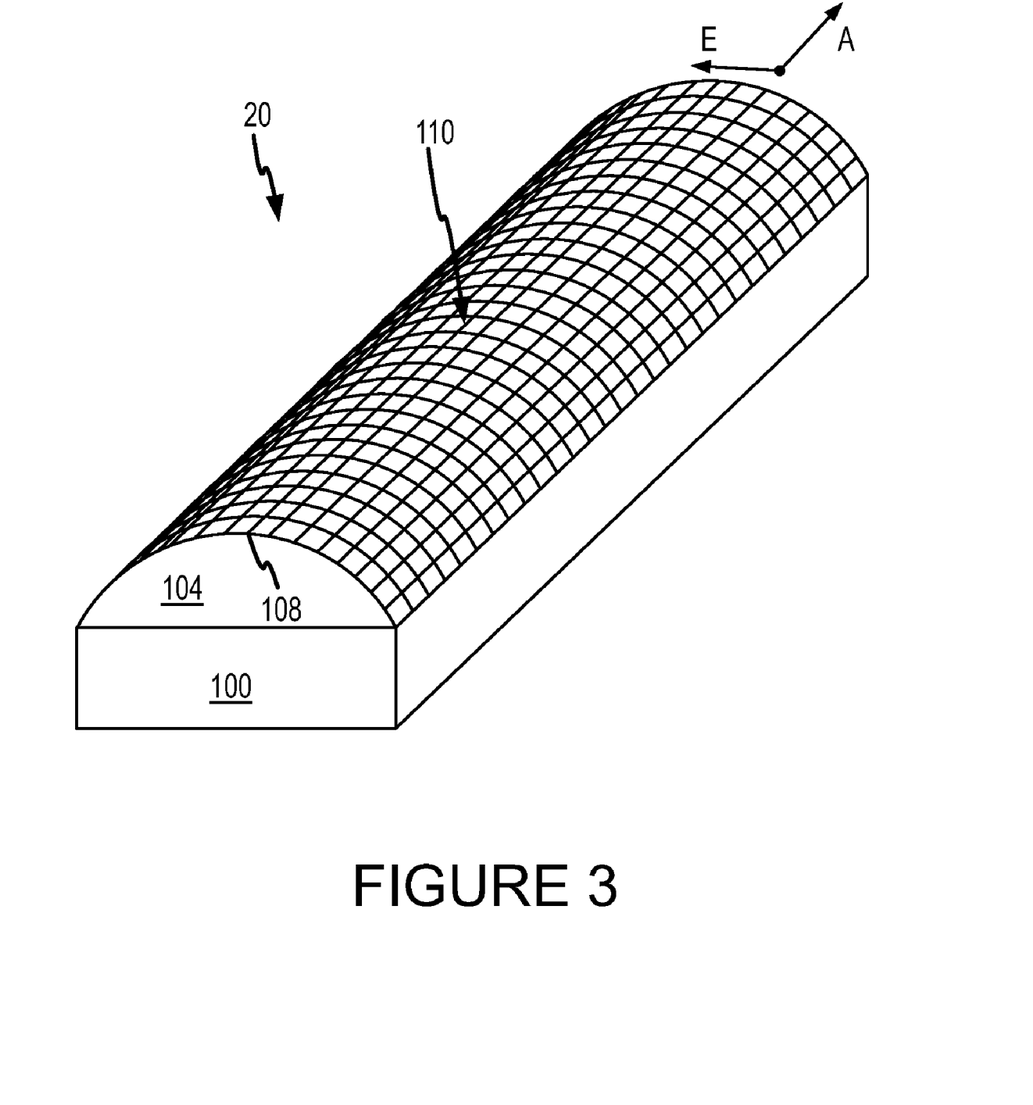
FIG. 3 is an isometric view of an ultrasound imaging probe according to one example of the invention that can be used in the imaging system of FIGS. 1 and 2.

One example of the ultrasound imaging probe 20 used in the system 10 is shown in FIG. 3. Of course, the probe 20 may be used in systems other than the system 10. The imaging probe 20 includes a base portion 100 that is rectangular in plan view as well as in azimuth "A" and elevation "E" elevational views. The base portion 100 will generally contain acoustic backing material to attenuate reverberations emanating from the back of the transducer array. Positioned above the base portion 100 is an array portion 104 that is rectangular in plan view and when viewed along the elevation direction, but curved when viewed along the azimuth direction. The array portion 104 has an array surface 108 that is curved or bowed outwardly in the elevation direction and is flat in the azimuth direction. A plurality of transducer elements, generally indicated by reference numeral 110, are located on the array surface 108. The transducer elements 110 are located on the array surface in rows extending in the azimuth direction and columns extending in the elevation direction.

The probe 20 can be fabricated using curved matrix array fabrication techniques. For example, one example involves thinning, tiling and curving application specific integrated circuits together in a flip chip array configuration. Another example is to fabricate an array of transducer elements on a flexible interposer and then attach the interposer to a curved backing block with embedded interconnects. Other techniques may also be used such as that shown in U.S. Pat. No. 6,043,590 (Gilmore).

Figure 4:
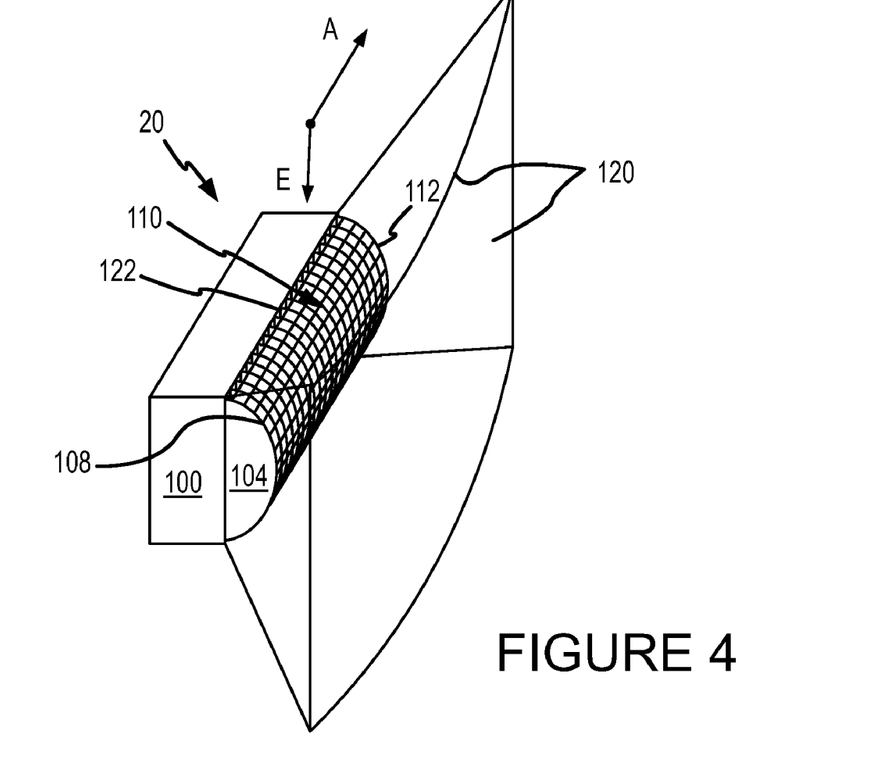
FIG. 4 is an isometric view of the ultrasound imaging probe of FIG. 3 showing its acoustic signal pattern.

The operation of the ultrasound imaging probe 20 and its acoustic pattern will now be explained with reference to FIG. 4. In operation, one or more columns of transducer elements 110 in the same azimuthal position are first scanned by transmitting ultrasound signals and receiving ultrasound echoes. For example, all of the transducer elements 110 in the end column 112 may first be scanned. Alternatively, the transducer elements 110 in the end column 112 and the transducer elements 110 in N columns adjacent the column 112 are first scanned. Scanning then proceeds in the azimuth direction in stepwise fashion from the elements 110 in one column or set of columns extending in the elevation direction to the next column or set of columns. As explained in greater detail below, delay units (not shown in FIG. 4) are used to delay electrical signals coupled to and from each of the transducer elements 110 to focus the transmitted and received ultrasound in elevation and/or azimuth in a selected direction and at a selected depth. In one example of the imaging probe 20, the delay units are not used to steer beams of transmitted and received ultrasound. Instead, scanning in the azimuth direction proceeds solely by stepping from one column or set of columns on a column-by-column basis. In another example of the probe 20, scanning in the azimuth direction proceeds by stepping on a column-by-column basis, but the delay units are steered at the ends of the image surface 108 so that the transmitted and received ultrasound extends from the probe 20 in the azimuth direction. The acoustic pattern 120 shown in FIG. 4 is created with a probe 20 using this example. In still another example of the probe 20, the delay units are used to steer the transmitted and received ultrasound in the azimuth and elevation directions. Steering the ultrasound in this manner will enlarge the field of view in both the azimuth and elevation directions, which is important in obstetrical imaging. The steering can allow the imaging system 10 to perform spatial compounding to reduce speckle artifact, as is well known in the art. Other examples may also be used.

As an alternative to stepping from scanning from column-to-column in the azimuth direction, scanning can be accomplished by stepping from row-to-row in the elevation direction. Using this approach, one or more rows of transducer elements 110 in the same elevational position are first scanned by transmitting ultrasound signals and receiving ultrasound echoes. For example, all of the transducer elements 110 in the end row 122 may first be scanned. Alternatively, the transducer elements 110 in the end row 122 and the transducer elements 110 in N rows adjacent the row 122 are first scanned. Scanning then proceeds in the elevation direction in stepwise fashion from one row to the next. As in the previous example, beams can be steered at angles which are off-axis (not orthogonal to the array surface) at the edges of the array in elevation, azimuth, or both in order to enlarge the field of view which is scanned by the array transducer.

The number of transducer elements 110 in the azimuth direction will depend upon the desired resolution and the size of the desired field of view in the near field. A fairly large number of transducer elements 110 may be required to provide an adequate field of view for certain application, such as obstetrical imaging. However, in the elevation direction, only a relatively few number of transducer elements 110 are required because the curvature of the array surface 120 in the elevation direction causes the transducer elements 110 to face at different angular increments in an arc in that direction. As a result, the acoustic pattern 120 shown in FIG. 4 also extends a substantial distance in the elevation direction despite the use of relatively few transducer elements in the elevation direction. The resulting acoustic pattern 120 thus has a very large aperture relative to conventional flat two-dimensional arrays having the same number of transducer elements. If desired, the delay elements can be used to steer the transmitted and received ultrasound off-axis in the elevation direction to increase the size of the field of view in that direction.

Figure 5:
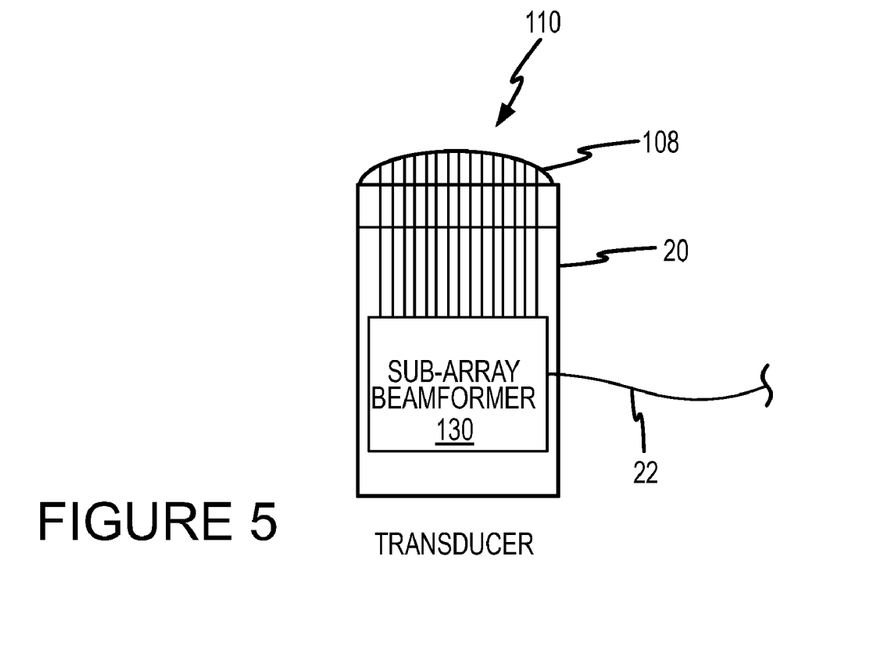
FIG. 5 is a schematic depiction of one example of electrical components used in the ultrasound imaging probe of FIG. 3.

The electrical components of the ultrasound imaging probe 20 are depicted schematically in FIG. 5. The probe 20 includes not only the transducer elements 110, but also sub-array beamformers 130. The sub-array beamformers 130 perform beamforming operations on sub-arrays of the transducer elements 110. The beamforming operations are performed on the signals received from the transducer elements 110 in the respective sub-array beamformer 130 by delaying the received signals and then combining the delayed signals into a composite signal. The ultrasound signal path 40 (FIG. 2) in the system 10 then performs further beamforming from the composite signals received from each of the sub-array beamformers 130. As a result, the number of signals that must be coupled from the probe 20 to the chassis 12 (FIG. 1), and hence the thickness of the cable 22, is further reduced from the reduction already achieved by using relatively fewer transducer elements 110 in the probe 20 to span the elevation direction.

Although the ultrasound imaging probe 20 shown in FIG. 5 uses a respective sub-array beamformer 130 for each sub-array of transducer elements, in other examples of the imaging probe 20 a respective sub-array beamformer 130 is provided only for each of the sub-arrays that will be simultaneously active. The active transducer elements 110 in each sub-array can then be multiplexed to a respective one of the sub-array beamformers. By having each sub-array beamformer 130 interface with multiple sub-arrays, the number of sub-array beamformers 130 can be reduced, albeit at the expense of adding multiplexers and multiplexer control circuits.

Figure 6:
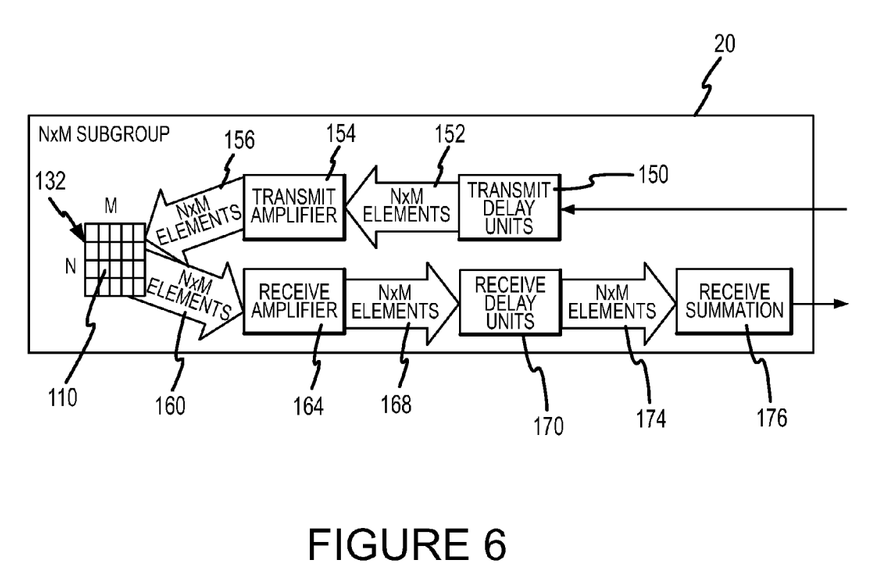
FIG. 6 is a block diagram of one of the sub-array beamformers used in the ultrasound imaging probe of FIG. 4 according to one example of the invention.

One of the sub-array beamformers 130 is shown in greater detail in FIG. 6. Each of the beamformers 130 services a sub-array 132 of transducer elements 110 containing M transducer elements extending in the elevation direction and N transducer elements extending in the azimuth direction. The ultrasound signal path 40 transmits a transmit waveform to the probe 20, which is received by transmit delay units 150, which were previously discussed. The ultrasound signal path may also send delay information to the sub-array beamformers. The transmit delay units 150 delay the transmit waveform by respective delay values to focus the ultrasound transmitted by the elements 110 to a selected depth, and optionally to steer the transmitted ultrasound in either or both of the azimuth and elevation directions. The resulting delayed signals are coupled through a bus 152 to a multi-channel transmit amplifier 154. The delayed signals are boosted by the amplifier 154 and applied through a bus 156 to respective transducer elements 110.

Electronic signals corresponding to acoustic echoes received by respective transducer elements are then coupled through a bus 160 to a multi-channel receive amplifier 164. The amplitude of the relatively low-level signals are increased by the receive amplifier 164 and applied through a bus 168 to receive delay units 170, which were also previously discussed. One of the received delay units 170 is provided for each signal received from a respective transducer element 110. The receive delay units 170 delay the amplified receive signal to focus the received ultrasound to a selected depth. The receive delay units 170 may also steer the received ultrasound in either or both of the azimuth and elevation directions. The delayed receive signals are coupled through a bus 174 to a summation circuit 176, which sums the signals from the receive delay units 170 to produce one composite signal from the sub-array of transducer elements. The instantaneous composite signal is indicative of the ultrasound received from a selected depth and location. The selected location may be beneath the center of the sub-array 132 or, if the receive delay units perform azimuth or elevation steering, the selected location may be offset from beneath the center of the sub-array 132.

Although the present invention has been described with reference to the disclosed examples, persons skilled in the art will recognize that changes may be made in form and detail without departing from the spirit and scope of the invention. For example, although the directional relationships of the ultrasound imaging probe 20 have been described with respect to azimuth and elevation directions, it will be understood that these assignments are somewhat arbitrary. The probe 20 could, for example, be considered to be flat in the elevation direction and curved outward in the azimuth direction. Also, while the transducer elements 110 have been described as being arranged in rows extending in the azimuth direction and columns extending in the elevation direction, this description is arbitrary, and the rows and columns could be considered to be arranged in the elevation and azimuth directions, respectively. Such modifications are well within the skill of those ordinarily skilled in the art. Accordingly, the invention is not limited except as by the appended claims.

I claim:

1. An ultrasound imaging probe, comprising:
a transducer body exhibiting a transmit beam origination pattern that is substantially flat in an azimuth direction and curved outward in an elevation direction;
a two-dimensional array of transducer elements mounted on the transducer body in rows extending in the azimuth direction and columns extending in the elevation direction;
a plurality of sub-array beamformers including delay units for beam steering coupled to respective sub-arrays of the transducer elements, each of the sub-array beamformers being operable to apply transmit signals to the transducer elements in the respective sub-array and to delay signals received from the transducer elements in the respective sub-array and to combine the delayed signals into a composite signal,
wherein the sub-array beamformers are operable apply the transmit signals to and receiving signals from the transducer elements in a stepping manner from one row or group of rows or one column or group of columns to the next;
wherein ones of the sub-array beamformers are further operable not to steer beams located away from the ends of the array so that beams are parallel to each other and orthogonal to the array surface;
wherein ones of the sub-array beamformers are further operable to steer in the azimuth direction ultrasound beams transmitted and received by transducer elements at the azimuthal ends of the array of transducer elements to be not orthogonal to the array surface, thereby causing the acoustic beam pattern of the probe to extend beyond the azimuthal ends of the array of transducer element;
wherein ones of the sub-array beamformers are further operable to steer in the elevation direction ultrasound beams transmitted and received by transducer elements at the elevation ends of the array of transducer elements to be not orthogonal to the array surface, thereby causing the acoustic beam pattern of the probe to extend beyond the elevation ends of the array of transducer elements; and
a communication link for coupling the composite signals to an ultrasound processing and display system.

2. The ultrasound imaging probe of claim 1 wherein the transmit beam origination pattern is curved outward in an elevation direction by a physical curvature of the array in the elevation direction.

3. The ultrasound imaging probe of claim 1 wherein the number of transducer elements in each row extending in the azimuth direction is substantially greater than the number of transducer elements in each columns extending in the elevation direction.

4. The ultrasound imaging probe of claim 1, further comprising an acoustic lens which acts to steer beams transmitted by the array,
wherein the transmit beam origination pattern is curved outward in an elevation direction by the steering of the acoustic lens in the elevation direction.

5. An ultrasound imaging system, comprising:
an ultrasound imaging probe, comprising:
a transducer body including an array transducer elements having rows of transducer elements that are substantially flat in an azimuth direction and columns of transducer elements that are curved outward in an elevation direction, the transducer elements transmitting beams which are steerable at orthogonal and non-orthogonal angles with respect to the surface of the array at their points of emanation;

wherein the ultrasound imaging probe further comprises a plurality of sub-array beamformers including delay units for beam steering coupled to respective sub-arrays of the transducer elements, each of the sub-array beamformers being operable to apply transmit signals to the transducer elements in the respective sub-array, each of the sub-array beamformers further being operable to delay signals received from the transducer elements in the respective sub-array and to combine the delayed signals into a composite receive signal;

wherein the delay units are operable not to steer beams located away from the ends of the array so that beams are parallel to each other and orthogonal to the array surface;

wherein the delay units are further operable to steer in the azimuth direction ultrasound beams transmitted and received by transducer elements at the azimuthal ends of the array of transducer elements to be not orthogonal to the array surface, thereby causing the acoustic beam pattern of the probe to extend beyond the azimuthal ends of the array of transducer element;

wherein the delay units are further operable to steer in the elevation direction ultrasound beams transmitted and received by transducer elements at the elevation ends of the array of transducer elements to be not orthogonal to the array surface, thereby causing the acoustic beam pattern of the probe to extend beyond the elevation ends of the array of transducer elements; and an ultrasound signal path applying transmit signals to and receiving signals from the transducer elements in the ultrasound imaging probe through a communications link, the ultrasound signal path combining the signals received from the transducer elements into image signals corresponding to an image of anatomical structures in a volumetric region adjacent the ultrasound imaging probe, wherein the ultrasound signal path is operable to apply the transmit signals to and receive signals from the transducer elements in a stepping manner from one row or group of rows or one column or group of columns to the next; and a display coupled to receive the image signals from the ultrasound signal path, the display being operable to show the volumetric image.

6. The ultrasound imaging system of claim 5 wherein each of the sub-array beamformers comprise:

a plurality of transmit delay units, each of the transmit delay units generating a respective transmit signal responsive to receipt of a transmit control signal;

a plurality of receive delay units, each of the receive delay units generating a respective delayed received signal; and a summing circuit combining the delayed received signals to provide a composite received signal.

7. The ultrasound imaging system of claim 5 wherein the ultrasound signal path is operable to perform spatial compounding on the receive signals from the transducer elements so that the display can show a spatially compounded volumetric image.

8. The ultrasound imaging system of claim 5 wherein a respective one of the sub-array beamformers is provided for each of the sub-arrays of the transducer elements.

9. The ultrasound imaging system of claim 5 wherein the number of transducer elements in each row extending in the azimuth direction is substantially greater than the number of transducer elements in each column extending in the elevation direction.

10. The ultrasound imaging system of claim 5 wherein the communications link comprises a multi-conductor cable.

11. A method of providing an image of anatomical structures in a volumetric region, the method comprising:

transmitting ultrasound into the volumetric region from a two-dimensional array of transducer elements in an ultrasound probe, the ultrasound being transmitted from the array in respective directions that, when steered orthogonal to the surface of the array, are parallel in the azimuth direction and diverging in the elevation direction, wherein transmitting ultrasound further comprises transmitting ultrasound from the elements of the array which are not near an end of the array which are not steered so as to be orthogonal to the surface of the array wherein transmitting ultrasound further comprises transmitting ultrasound from the elements of the array near an azimuthal end of the array to be not orthogonal to the surface of the array and in a direction that diverges in the azimuth direction from the direction orthogonal to the array wherein transmitting ultrasound further comprises transmitting ultrasound from the elements of the array near an elevational end of the array to be not orthogonal to the surface of the array and in a direction that diverges in the elevation direction from the direction orthogonal to the array;

receiving ultrasound echoes from the volumetric region with the two-dimensional array;

processing the received echoes with sub-array beamformers located in the probe and coupled to sub-arrays of the transducer elements;

coupling the processed echoes to an ultrasound image processing and display system;

further transmitting and receiving signals from the transducer elements in a stepping manner from one row or group of rows of the two-dimensional array or one column or group of columns of the two-dimensional array to the next; and processing the processed echoes to create an image of anatomical structures in the volumetric region.

* * * * *